United States Patent
Xue

(10) Patent No.: US 11,952,593 B2
(45) Date of Patent: Apr. 9, 2024

(54) DETECTION AND TREATMENT OF DAUGHTER NUMBER VARIATIONS IN CANCER CELLS

(71) Applicant: PharmacoGenetics Limited, Shatin (CN)

(72) Inventor: Hong Xue, Hong Kong (CN)

(*) Notice: Subject to any disclaimer, the term of this patent is extended or adjusted under 35 U.S.C. 154(b) by 50 days.

(21) Appl. No.: 17/495,768

(22) Filed: Oct. 6, 2021

(65) Prior Publication Data
US 2022/0105071 A1    Apr. 7, 2022

Related U.S. Application Data

(60) Provisional application No. 63/087,903, filed on Oct. 6, 2020.

(51) Int. Cl.
| | | |
|---|---|---|
| *C12N 5/09* | (2010.01) | |
| *C12Q 1/02* | (2006.01) | |
| *G01N 21/64* | (2006.01) | |
| *G01N 33/50* | (2006.01) | |

(52) U.S. Cl.
CPC ....... *C12N 5/0693* (2013.01); *G01N 21/6458* (2013.01); *G01N 33/5011* (2013.01); *C12N 2501/06* (2013.01); *C12Q 1/025* (2013.01)

(58) Field of Classification Search
CPC .............. C12N 5/0693; C12N 2501/06; G01N 21/6458; G01N 33/5011
See application file for complete search history.

(56) References Cited

U.S. PATENT DOCUMENTS

2003/0104461 A1* 6/2003 Muehlbauer ....... G01N 33/5044
435/6.12

OTHER PUBLICATIONS

Rengstl et al., "Incomplete cytokinesis and re-fusion of small mononucleated Hodgkin cells lead to giant multinucleated Reed-Sternberg cells," Proc Natl Acad Sci U.S.A. 110(51): 20729-34. doi: 10.1073/pnas.1312509110. Epub Dec. 3, 2013. (Year: 2013).*
Mirzayans et al., "Roles of Polyploid/Multinucleated Giant Cancer Cells in Metastasis and Disease Relapse Following Anticancer Treatment," Cancers 10(4): 118. doi: 10.3390/cancers10040118. (Year: 2018).*
Krishna et al., "Asynchrony of nuclear development in cytochalasin-induced multinucleate cells," J Cell Biol 43(3): 618-621. doi: 10.1083/jcb.43.3.618. (Year: 1969).*
Chung et al., "Anticancer effects of wogonin in both estrogen receptor-positive and -negative human breast cancer cell lines in vitro and in nude mice xenografts," International Journal of Cancer 122(4): 816-22. doi: 10.1002/ijc.23182. First published: Oct. 23, 2007 (Year: 2007).*
White-Gilbertson et al., "Tamoxifen is a candidate first-in-class inhibitor of acid ceramidase that reduces amitotic division in polyploid giant cancer cells—Unrecognized players in tumorigenesis," Cancer Med. 9(9): 3142-3152. doi: 10.1002/cam4.2960. Epub Mar. 5, 2020. (Year: 2020).*
Mascaraque et al., "Mitotic Catastrophe Induced in HeLa Tumor Cells by Photodynamic Therapy with Methyl-aminolevulinate," Int J Mol Sci 205(5): 1229. doi: 10.3390/ijms20051229. (Year: 2019).*
Tyagi, I., et al., "Intrinsic and Chemically Induced Daughter Number Variations In Cancer Cell Lines," Cell Cycle, 2021, pp. 537-549, vol. 20, Nos. 5-6.

* cited by examiner

*Primary Examiner* — Tracy Vivlemore
*Assistant Examiner* — Eric J Rogers

(57) ABSTRACT

The present disclosure provides in vitro methods for predicting a compound's ability to inhibit multinucleate cell production resulting from post-mitotic cell fusion during a process of Daughter Number Variation (DNV) in mitosis. Compounds identified by this method can be used in cancer treatment, either alone or in combination with other known cancer drugs. The present invention also provides methods of personalized cancer treatment for a patient having a malignant tumor.

20 Claims, 8 Drawing Sheets
(6 of 8 Drawing Sheet(s) Filed in Color)

Figure 4

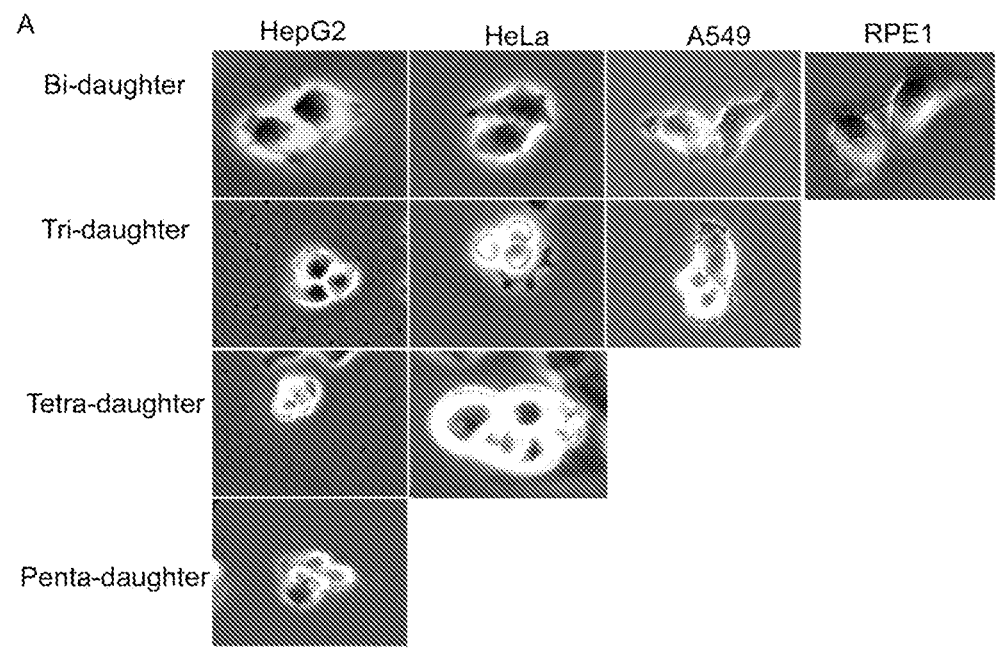

B

HepG2

| Treatment | Neutral | Acidic | Alkaline | Wogonin | 5-FU |
|---|---|---|---|---|---|
| Bi-daughter | +++ | +++ | +++ | +++ | +++ |
| Tri-daughter | + | +++ | ++ | +++ | +++ |
| Tetra-daughter | + | ++ | + | +++ | + |
| Penta-daughter | + | + | - | + | - |

HeLa

| Treatment | Neutral | Acidic | Alkaline | Wogonin | 5-FU |
|---|---|---|---|---|---|
| Bi-daughter | +++ | +++ | +++ | +++ | +++ |
| Tri-daughter | ++ | +++ | ++ | +++ | +++ |
| Tetra-daughter | + | + | + | + | + |
| Penta-daughter | - | - | - | - | - |

A549

| Treatment | Neutral | Acidic | Alkaline | Wogonin | 5-FU |
|---|---|---|---|---|---|
| Bi-daughter | +++ | +++ | +++ | +++ | +++ |
| Tri-daughter | + | +++ | + | ++ | + |
| Tetra-daughter | - | - | - | - | - |
| Penta-daughter | - | - | - | - | - |

RPE1

| Treatment | Neutral | Acidic | Alkaline | Wogonin | 5-FU |
|---|---|---|---|---|---|
| Bi-daughter | +++ | +++ | +++ | +++ | +++ |
| Tri-daughter | - | - | - | - | - |
| Tetra-daughter | - | - | - | - | - |
| Penta-daughter | - | - | - | - | - | ated by reference.
DETECTION AND TREATMENT OF DAUGHTER NUMBER VARIATIONS IN CANCER CELLS

CROSS REFERENCE TO RELATED APPLICATIONS

This application claims the benefit of U.S. Provisional Patent Application No. 63/087,903 filed Oct. 6, 2020. The entire contents of the above application are hereby incorporated by reference.

FIELD OF THE INVENTION

The present disclosure provides in vitro methods for predicting a compound's ability to inhibit multinucleate cell production resulting from cell fusion during a process of Daughter Number Variation (DNV) in mitosis. These methods utilize known compounds for treating cancer or any test compounds. Also provided are methods of personalized cancer treatment for patients having malignant tumors, which use the in vitro methods for predicting a compound's ability to inhibit multinucleate cell production resulting from cell fusion during DNV in mitosis.

BACKGROUND OF THE INVENTION

In normal cell division, a mitotic mother cell produces two daughter cells, each with a single cell nucleus. Aberrant mitosis contributes to cancers through the accumulation of genetic abnormalities that favor cancer development (Gisselsson D. *Chromosome* 2008; 117(6):511-519; McClelland S E. Endocr Relat Cancer. 2017; 24(9):23-31; Duncan et al. Nature. 2010; 467(7316):707-710), and that increase genotypic and phenotypic diversity in the tumor population (Beach et al. *Cell* 2017; 169:229-242.e21). A multipolar mitosis is an aberrant form of mitosis, wherein the chromosomal material is pulled to more than two poles. This is typically associated with an increase in centrosome number since the centrosome is an organelle that serves as the main microtubule organizing center (MTOC) of the animal cell, as well as a regulator of cell-cycle progression. Multipolar mitoses have been detected in numerous cancer cells, and can give rise to multinucleate cells.

Multi-daughter cell divisions have been detected in malignant tumors since the 1890's (Hansemann V. *Arch Pathol Anat Physiol Klin Medicin.* 1890; 119(119):209-236), and as shown previously, more than 3% of mitotic cells in the SGB4 glioblastoma cell line underwent multipolar mitosis to yield viable daughter cells that completed several rounds of mitosis (Telentschak et al. *Oncol Rep.* 2015 April; 33(4): 2001-8). Inductions of mitotic anomalies including multipolar division, asymmetric division, and cell fusion were observed in HeLa cells under mechanical compression (Tse et al. PloS one. 2012; 7(6); Kittur et al., *Biomed Microdevices.* 2014 Jun. 1; 16(3):439-447). Similarly, exposure to asbestos caused multipolar mitosis and aneuploidy formation in various types of cultured mammalian cells (Cortez et al. *Oncotarget.* 21 2016; 7(8):8979-8992; Zhang et al. *Oncotarget.* 2017; 8(7):11030-11041; Cortez et al. *PloS one.* 2011; 6(4):e18600-e18600), and both heat stress and ionizing radiation brought about mitotic catastrophes in U2OS osteosarcoma cells with multiple centrosomes (Chen et al. *Cells* 2019; 8(8):888; Dodson et al. *Cell Cycle.* 2007; 6(3):364-370). Similarly, short exposure to paclitaxel treatment resulted in the generation of multipolar spindle (Bian et al. *Sci China Life Sci.* 2010; 53(11):1322-1329; Zasadil et al. *Sci Transl Med.* 2014; 6(229):229ra43-229ra43), and carboplatin and dinaciclib induced multipolar spindle formation and aneuploidy (Rohnalter et al. *Oncotarget.* 4 2015; 6(37):40005-40025; Danilov et al. *Mol Cancer Thor.* 2016; 15(11):2758-2766). Thus, multinucleate cancer cells are known to generate aneuploidy that enhances the aggressiveness, metastasis and drug resistance of cancers.

SUMMARY OF THE INVENTION

An in vitro method for predicting a compound's ability to inhibit multinucleate cell production resulting from cell fusion during a process of Daughter Number Variation (DNV) in mitosis is provided. The method comprises:
  culturing cancer cells in the presence or absence of the compound for a predetermined period of time;
  identifying cell subgroups P1 through P8 in DNV; and
  counting numbers of P1 and/or (P1 and P2) cell subgroups and P3 through P8 cell subgroups produced during the predetermined period of time in the presence or absence of the compound, wherein a larger proportion of the P1 and/or (P1 and P2) cell subgroups of the total number of P1 through P8 cell subgroups in the cancer cells cultured in the presence of the compound as compared to the proportion of the P1 and/or (P1 and P2) cell subgroups of the total number of P1 through P8 cell subgroups in the cancer cells cultured in the absence of the compound predicts the compound's ability to inhibit the multinucleate cell production resulting from post-mitotic cell fusion during DNV,
  wherein P1 cell subgroups are single mononucleate cells, P2 cell subgroups are clusters of one binucleate cell and two mononucleate cells, P3 cell subgroups are clusters of one multinucleate cell with two nuclei and one mononucleate cell, P4 cell subgroups are one multinucleate cell with three nuclei, P5 cell subgroups are clusters of either two multinucleate cells with two nuclei or one multinucleate cell with two nuclei and one binucleate cell, P6 cell subgroups are clusters of one multinucleate cell with three nuclei and one mononucleate cell, P7 cell subgroups are one multinucleate cell with four nuclei, and P8 cell subgroups are one multinucleate cell with five nuclei; and
  wherein P1 and P2 cell subgroups have not undergone post-mitotic cell fusion and P3 through P8 cell subgroups have undergone post-mitotic cell fusion.

This method can further comprise:
  culturing cancer cells in the presence or absence of a known compound for a predetermined period of time;
  identifying cell subgroups P1 through P8 in DNV; and
  counting numbers of P1 and/or (P1 and P2) cell subgroups and P3 through P8 cell subgroups produced during the predetermined period of time in the presence or absence of the known compound, wherein a larger proportion of the P1 and/or (P1 and P2) cell subgroups of the total number of P1 through P8 cell subgroups in the cancer cells cultured in the presence of the known compound as compared to the proportion of the P1 and/or (P1 and P2) cell subgroups of the total number of P1 through P8 cell subgroups in the cancer cells cultured in the absence of the known compound predicts the compound's ability to inhibit the multinucleate cell production resulting from post-mitotic cell fusion during DNV; and
  wherein the compound is identified as a treatment for cancer if the compound's ability to inhibit the multinucleate cell production resulting from post-mitotic cell fusion during DNV is greater than or equal to the known compound's ability to inhibit the multinucleate cell production resulting from post-mitotic cell fusion during DNV.

A method of treating cancer in a patient having a tumor is also provided, wherein the method comprises administering a compound to the patient, wherein the compound was identified by the above in vitro method.

Further provided is a method of personalized cancer treatment for a patient having a malignant tumor, the method comprising:

culturing cancer cells in the presence or absence of a test compound for a predetermined period of time;

identifying cell subgroups P1 through P8 in DNV; and counting numbers of P1 and/or (P1 and P2) cell subgroups and P3 through P8 cell subgroups produced during the predetermined period of time in the presence or absence of the test compound, wherein a larger proportion of the P1 and/or (P1 and P2) cell subgroups of the total number of P1 through P8 cell subgroups in the cancer cells cultured in the presence of the compound as compared to the proportion of the P1 and/or (P1 and P2) cell subgroups of the total number of P1 through P8 cell subgroups in the cancer cells cultured in the absence of the test compound predicts the compound's ability to inhibit the multinucleate cell production resulting from post-mitotic cell fusion during DNV;

repeating the culturing, identifying and counting steps for one or more additional test compounds for treating cancer, and administering to the patient the test compound for treating cancer identified as having the greatest ability to inhibit the multinucleate cell production resulting from post-mitotic cell fusion during DNV in combination with at least one cytotoxic anticancer drug, wherein P1 cell subgroups are single mononucleate cells, P2 cell subgroups are clusters of one binucleate cell and two mononucleate cells, P3 cell subgroups are clusters of one multinucleate cell with two nuclei and one mononucleate cell, P4 cell subgroups are one multinucleate cell with three nuclei, P5 cell subgroups are clusters of either two multinucleate cells with two nuclei or one multinucleate cell with two nuclei and one binucleate cell, P6 cell subgroups are clusters of one multinucleate cell with three nuclei and one mononucleate cell, P7 cell subgroups are one multinucleate cell with four nuclei, and P8 cell subgroups are one multinucleate cell with five nuclei; and wherein P1 and P2 cell subgroups have not undergone post-mitotic cell fusion and P3 through P8 cell subgroups have undergone post-mitotic cell fusion.

The present disclosure additionally provides a method of personalized cancer treatment for a patient having a malignant tumor, wherein the method comprises;

culturing cancer cells in the presence or absence of a test compound and at least one anticancer drug for a predetermined period of time;

identifying cell subgroups P1 through P8 in DNV; and counting numbers of P1 and/or (P1 and P2) cell subgroups and P3 through P8 cell subgroups produced during the predetermined period of time in the presence or absence of the test compound and the at least one anticancer drug, wherein a larger proportion of the P1 and/or (P1 and P2) cell subgroups of the total number of P1 through P8 cell subgroups in the cancer cells cultured in the presence of the compound and the at least one anticancer drug as compared to the proportion of the P1 and/or (P1 and P2) cell subgroups of the total number of P1 through P8 cell subgroups in the cancer cells cultured in the absence of the test compound and the at least one anticancer drug predicts the compound's ability to inhibit the multinucleate cell production resulting from post-mitotic cell fusion during DNV;

repeating the culturing, identifying and counting steps for one or more additional test compounds for treating cancer; and administering to the patient the test compound for treating cancer identified as having the greatest ability to inhibit the multinucleate cell production resulting from post-mitotic cell fusion during DNV in combination with the at least one anticancer drug;

wherein P1 cell subgroups are single mononucleate cells, P2 cell subgroups are clusters of one binucleate cell and two mononucleate cells, P3 cell subgroups are clusters of one multinucleate cell with two nuclei and one mononucleate cell, P4 cell subgroups are one multinucleate cell with three nuclei, P5 cell subgroups are clusters of either two multinucleate cells with two nuclei or one multinucleate cell with two nuclei and one binucleate cell, P6 cell subgroups are clusters of one multinucleate cell with three nuclei and one mononucleate cell, P7 cell subgroups are one multinucleate cell with four nuclei, and P8 cell subgroups are one multinucleate cell with five nuclei; and wherein P1 and P2 cell subgroups have not undergone post-mitotic cell fusion and P3 through P8 cell subgroups have undergone post-mitotic cell fusion.

Other objects and features will be in part apparent and in part pointed out hereinafter.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4 shows types of daughter number variations observed in different cell lines under varied treatment conditions. Panel A: Phase contrast photos 1 of bi-daughter, tri-daughter, tetra-daughter and penta-daughter cell divisions under different treatment conditions. Panel B: Different extents of multi-daughter production where +++ represents greater than 0.4% of total mitotic divisions; ++ represents between 0.30-0.39%; + represents less than 0.29%; and '–' represents absence of any division. Magnification ×100, with 10 μm scale bars.

DEFINITIONS

Figure 1:
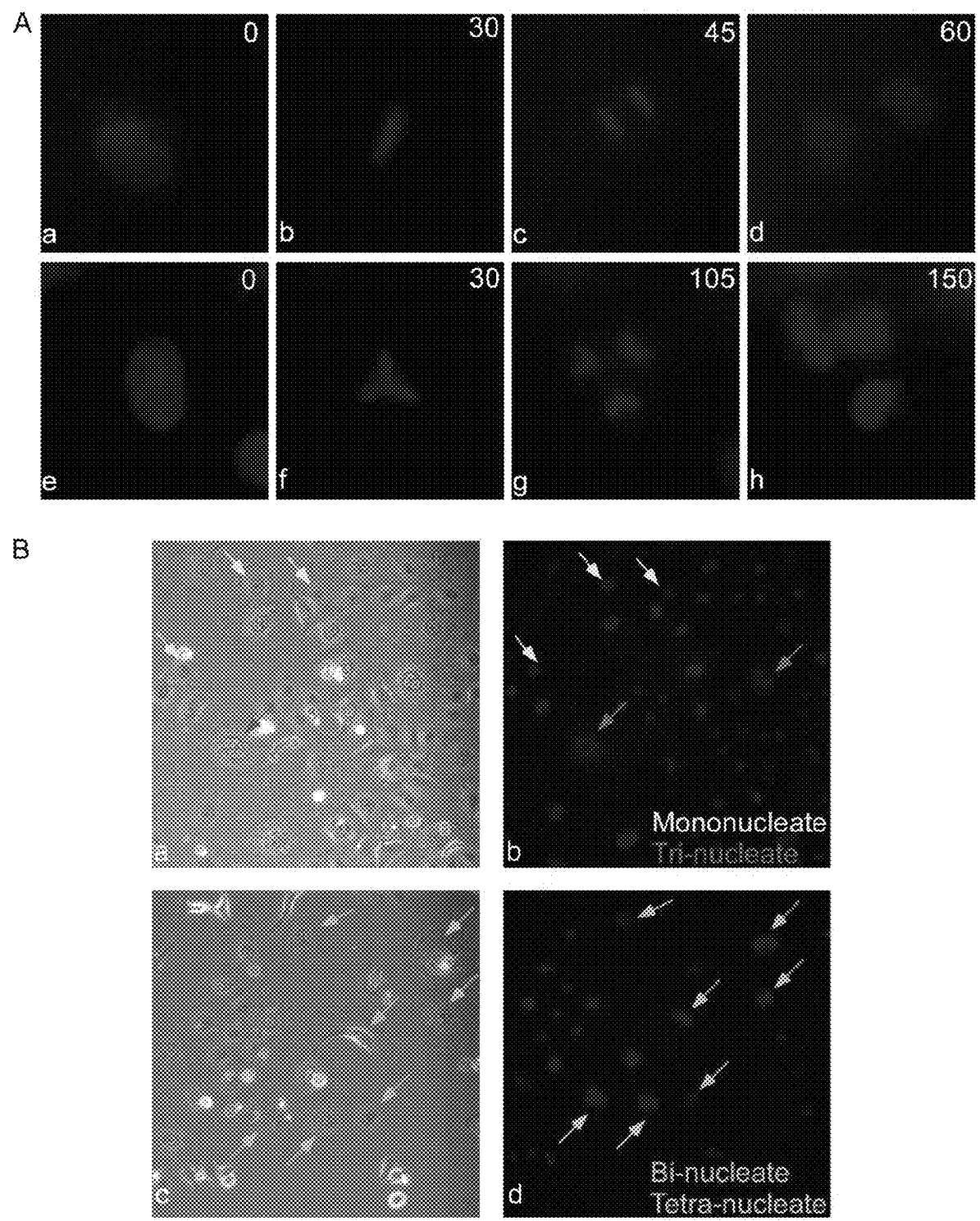
FIG. 1 depicts DNVs as illustrated by mitoses of HeLa cells under neutral pH conditions. Panel A (a-d): Mother cell in mitosis, successively reaching metaphase at 30 minutes, anaphase at 45 minutes, and two daughter cells at 60 minutes (cells shown in blue). Panel A (e-h): Mother cell in multi-daughter mitosis reaching metaphase at 30 minutes, anaphase at 105 minutes and three daughter cells at 150 minutes. Fluorescence microscopy at 100× magnification. Panel B: Photos with phase contrast (left panels), and with fluorescence (right panels; cells shown in blue) microscopy. Yellow, green, red and aqua blue arrows pointing to mono-nucleate, tri-nucleate, bi-nucleate and tetra-nucleate cells, respectively.

The terms "treatment", "treating" and the like are used herein to generally mean obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease or in delaying the disease. "Treatment" or "treating" or the like as used herein covers any treatment of a disease or symptom in a mammal, and includes: (a) preventing the disease or symptom from occurring in a subject who may be predisposed to acquiring the disease or symptom but has not yet been diagnosed as having it; (b) inhibiting the disease or symptom, i.e., arresting its development; or (c) relieving the disease, i.e., causing regression of the disease. Inhibiting or preventing a symptom means that an improvement is observed in the subject with respect to symptoms associated with the underlying disease, notwithstanding that the subject may still be afflicted with the underlying disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pies, horses, goats, and the like), etc.

It is noted that as used herein and in the appended claims, the singular forms "a," "an," and "the" include plural referents unless the context clearly dictates otherwise. Thus, for example, reference to "a cancer cell line" includes a multitude of such cell lines.

As used herein, the term "administering," refers to the delivery of a composition as disclosed herein into a subject by a method or route which results in at least partial delivery of the agent to the subject. The compositions disclosed herein can be administered by any appropriate route which results in an effective treatment in the subject, for example by intravenous, intramuscular or oral route.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable sub-combination. All combinations of the embodiments pertaining to the invention are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

DETAILED DESCRIPTION OF THE INVENTION

The present disclosure provides a number of methods related to in vitro methods for predicting a compound's ability to inhibit multinucleate cell production resulting from cell fusion during a process of Daughter Number Variation (DNV) in mitosis. Methods of personalized cancer treatment for a patient having a malignant tumor and for treating cancer, which utilize these in vitro methods are also provided.

"Daughter Number Variation" is a process that occurs during mitosis, where more than two daughter cells are produced per mitotic division. It is a two-stage process, wherein cell divisions of mono-nucleate, bi-nucleate, tri-nucleate and tetra-nucleate mother cells at Stage 1 produce subgroups of single mono-nucleate cells (herein referred to as P1), and subgroups containing one bi-nucleate cell and two mono-nucleate cells (herein referred to as P2). Stage 1 is followed by Stage 2, during which time some of the daughter cells from Stage 1 fuse to produce multi-nucleate cell subgroups, where the different subgroups differ with respect to the number of constituent cells and their nucleate status (herein referred to as P3 through P8). All the subgroups from a single DNV mitosis stay close to one another to form a distinct cluster when the cell culture is not overly dense with cells.

P1 subgroup cells are daughter mono-nucleate cells resulting from mitoses with DNV that have not undergone any post-mitotic cell fusion. P2 subgroup daughter cells are clusters of one bi-nucleate cell and two mono-nucleate cells, which also have not undergone any post-mitotic cell fusion during DNV, whereas each of the multi-nucleated subgroups contains at least one cell that is generated from post-mitotic fusions between the Stage 1 cells. P3 through P8 are daughter cell subgroups, which result from cell fusions during DNV, and wherein each subgroup includes at least one multinucleate cell.

Figure 2:
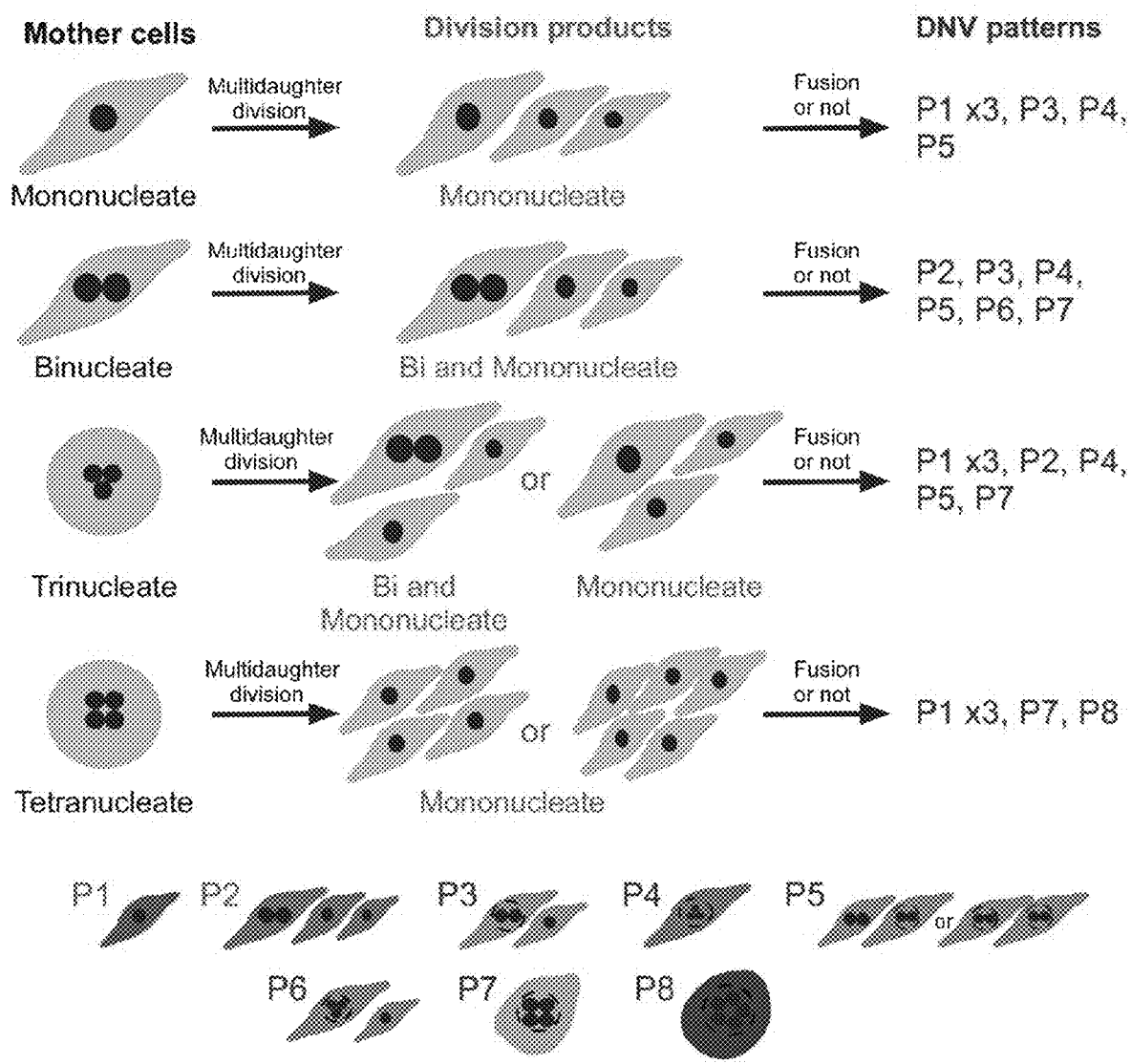
FIG. 2 depicts multi-daughter production by mother cells with different ploidies showing the ploidy patterns of cell division products in Stage 1, and the DNV ploidy patterns at the end of Stage 2. The mother cells (shown in purple) divide into binucleate and/or mononucleate daughter cells (shown in green) and further post-mitotic cell fusion can result (shown in red; cell subgroups are P1 (pink); P2 (blue); P3 (green); P4 (orange); P5 (light blue); P6 (gray); P7 (orchid) and P8 (magenta)).
Figure 3:
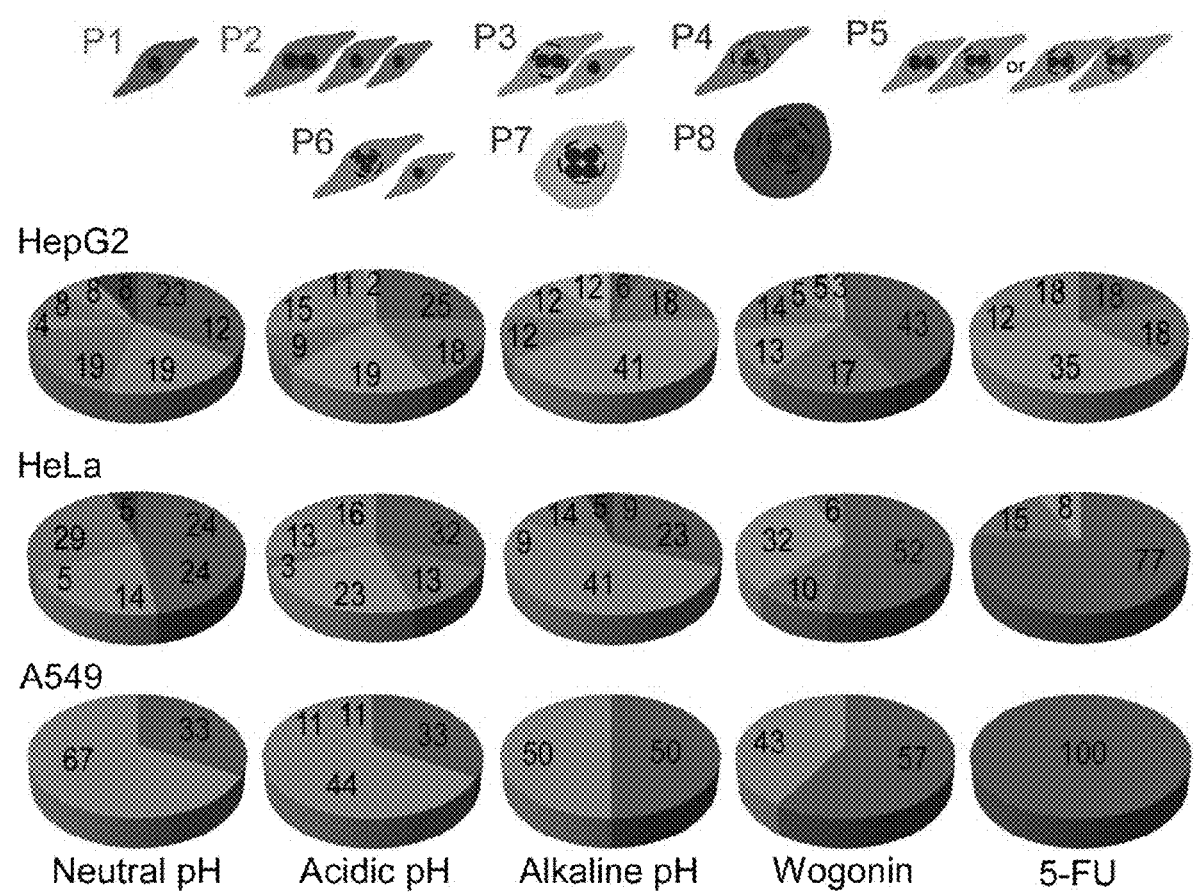
FIG. 3 depicts pie diagrams of the percentages of P1 through P8 patterns in HepG2, HeLa and A549 under varied treatment conditions respectively, as shown in Table 4 (cell subgroups are P1 (pink); P2 (blue); P3 (green); P4 (orange); P5 (light blue); P6 (gray); P7 (orchid) and P8 (magenta)).
Figure 5:
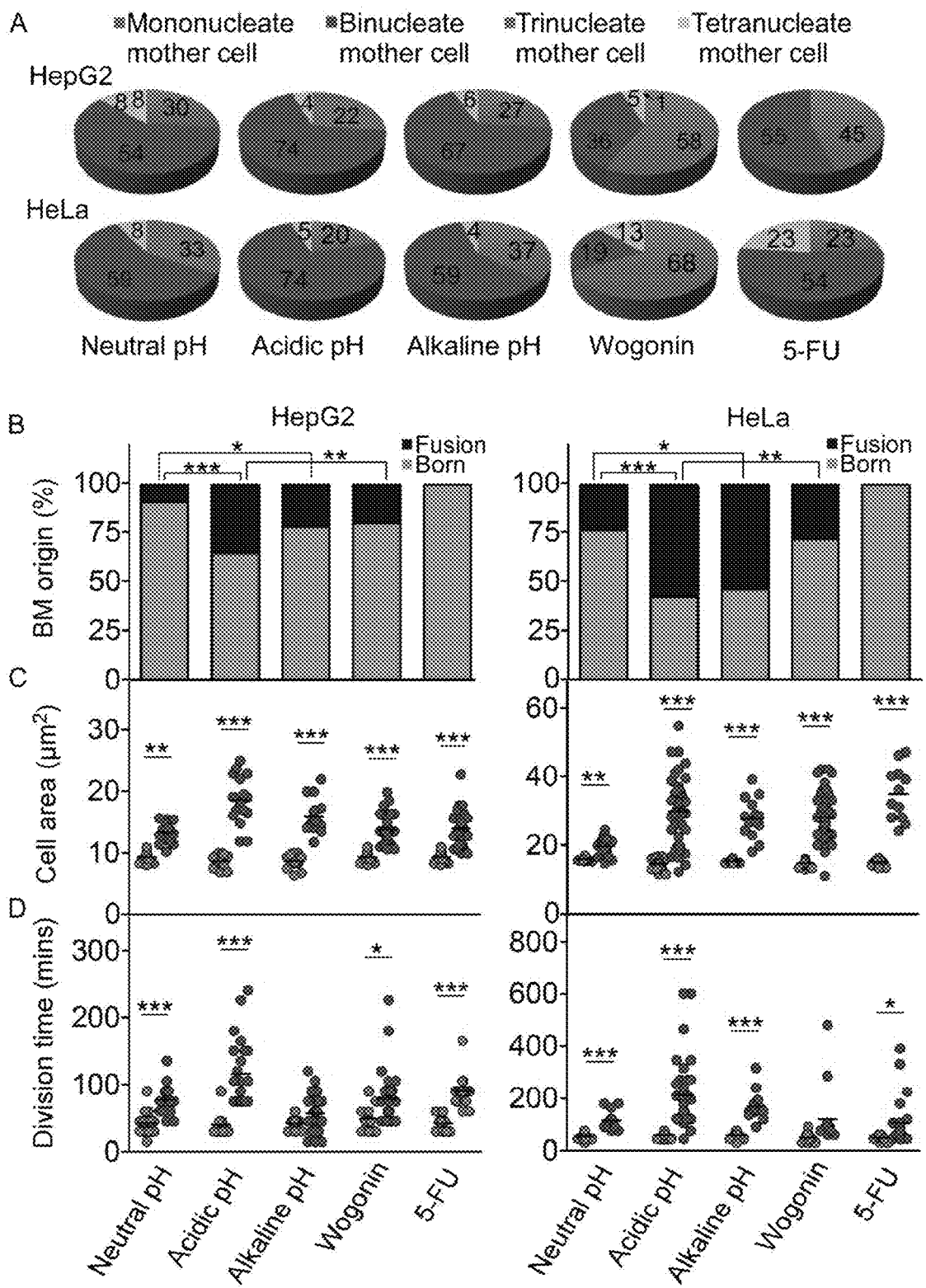
FIG. 5 shows mother cell characteristics. Panel A: Percentages of mother cells containing different numbers of nuclei. (mother cells are: mononucleate (blue), binucleate (red), trinucleate (green) or tetranucleate (yellow). Panel B: Fusion origin versus born origins of binucleate mother (BM) cells found under the different treatment conditions as indicated on x-axis below Part D (fusion origin (blue), born origin (light blue). Panel C: Cell area of bi-daughters (i.e., normal division, green circle) and multi-daughter (i.e., yielding three or more daughters in Stage 1, red circle) mother cells under different treatment conditions. Panel D: Division times exhibited by bi-daughter (green circle) and multi-daughter (red circle) mother cells under different treatment conditions. Statistical analysis was performed using binomial distribution in Panel B, and t test with Graphpad prism software in Panels C and D (*$p<0.05$, $p<0.001$ and $p<0.0001$). All data sets were derived from three independent experiments, and the mean is represented by horizontal bar.
Figure 6:
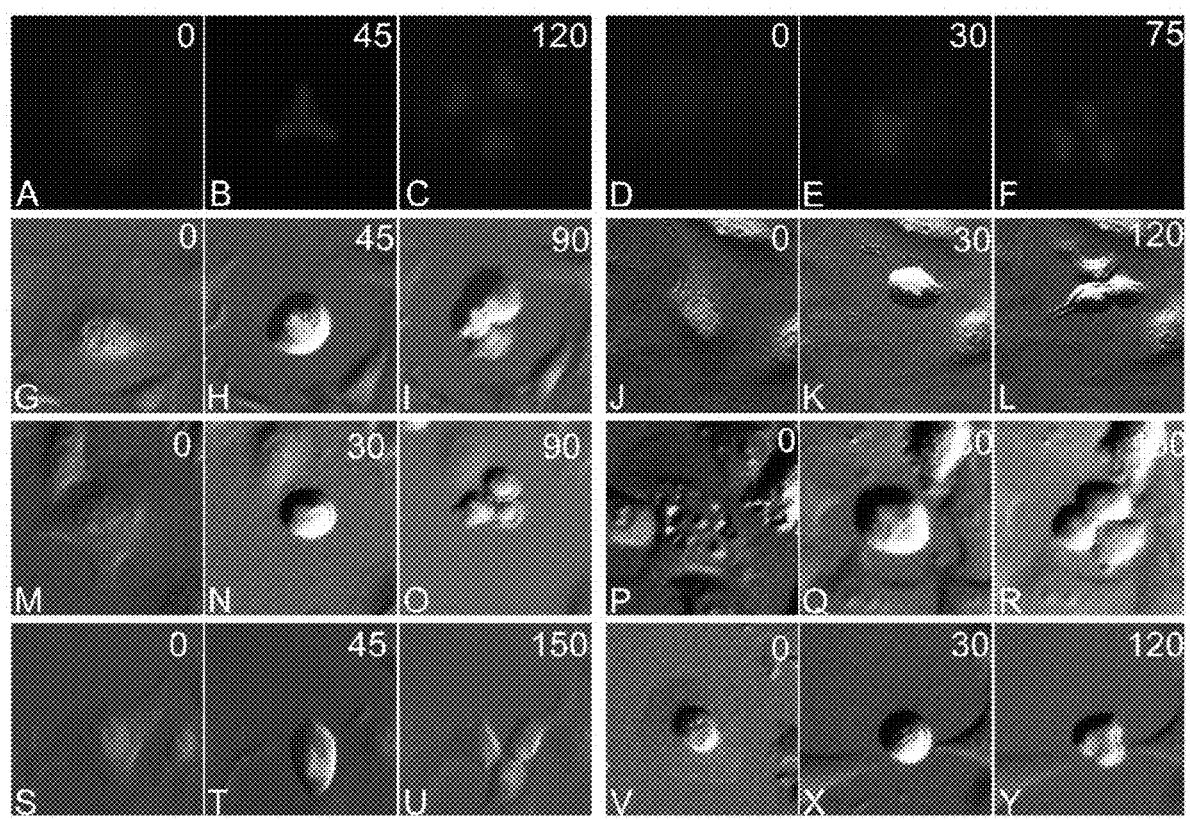
FIG. 6 depicts DNVs in HeLa, HepG2 and A549 cell lines under different treatment conditions. Three panels showing mother cell, reaching anaphase and producing three daughter cells: (A-C) HepG2 mononucleate mother cell at acidic pH; (D-F) A549 mononucleate mother cell at acidic pH; (G-1) HeLa binucleate mother cell under wogonin treatment; (J-L) HepG2 mononucleate mother cell under wogonin treatment; (M-O) A549 mononucleate mother cell under wogonin treatment; (P-R) HeLa mononucleate mother cell under 5-FU treatment; (S-U) HepG2 mononucleate mother cell under 5-FU treatment; (V-Y) A549 mononucleate mother cell under 5-FU treatment.

By way of example and not of limitation, there is at least one multinucleate cell with two nuclei in P3 and P5, one multinucleate cell with three nuclei in P4 and P6, one multinucleate cell with four nuclei in P7, and one multinucleate cell with five nuclei in P8, sharing the same cytoplasm. More specifically, P3 cell subgroups are clusters of one multinucleate cell with two nuclei and one mononucleate cell, P4 cell subgroups are one multinucleate cell with three nuclei, P5 cell subgroups are clusters of either two multinucleate cells with two nuclei or one multinucleate cell with two nuclei and one binucleate cell, P6 cell subgroups are clusters of one multinucleate cell with three nuclei and one mononucleate cell, P7 cell subgroups are one multinucleate cell with four nuclei, and P8 cell subgroups are one multinucleate cell with five nuclei. P1 through P8 cell subgroups are depicted in detail in FIG. 2.

Different cancer cells and cell lines may exhibit different combinations of multi-nucleated cell subgroups, or additional ones beyond P3 through P8. For instance, and as noted in the Examples, HepG2 and Hela cancer cell lines gave rise to tetra-ploid (i.e., tetra-nucleate) daughters during DNV, whereas A649 cell line did not.

A skilled artisan can readily determine multi-nucleate subgroups of cells that result from cell fusion during DNV based on the methods described herein. The in vitro methods provided herein are based on P1 and/or (P1 and P2) subgroups described above, which can be readily distinguished from any of the other subgroups of multi-nucleated cells.

The present disclosure provides an in vitro method for predicting a compound's ability to inhibit multinucleate cell production resulting from cell fusion during a process of Daughter Number Variation (DNV) in mitosis, wherein the method comprises:

culturing cancer cells in the presence or absence of the compound for a predetermined period of time;

identifying cell subgroups P1 through P8 in DNV; and counting numbers of P1 and/or (P1 and P2) cell subgroups and P3 through P8 cell subgroups produced during the predetermined period of time in the presence or absence of the compound, wherein alarger proportion of the P1 and/or (P1 and P2) cell subgroups of the total number of P1 through P8 cell subgroups in the cancer cells cultured in the presence of the compound as compared to the proportion of the P1 and/or (P1 and P2) cell subgroups of the total number of P1 through P8 cell subgroups in the cancer cells cultured in the absence of the compound predicts the compound's ability to inhibit the multinucleate cell production resulting from post-mitotic cell fusion during DNV, wherein P1 cell subgroups are single mononucleate cells, P2 cell subgroups are clusters of one binucleate cell and two mononucleate cells, P3 cell subgroups are clusters of one multinucleate cell with two nuclei and one mononucleate cell, P4 cell subgroups are one multinucleate cell with three nuclei, P5 cell subgroups are clusters of either two multinucleate cells with two nuclei or one multinucleate cell with two nuclei and one binucleate cell, P6 cell subgroups are clusters of one multinucleate cell with three nuclei and one mononucleate cell, P7 cell subgroups are one multinucleate cell with four nuclei, and P8 cell subgroups are one multinucleate cell with five nuclei; and wherein P1 and P2 cell subgroups have not undergone post-mitotic cell fusion and P3 through P8 cell subgroups have undergone post-mitotic cell fusion.

This in vitro method can further comprise:

culturing cancer cells in the presence or absence of a known compound for a predetermined period of time;

identifying cell subgroups P1 through P8 in DNV; and counting numbers of P1 and/or (P1 and P2) cell subgroups and P3 through P8 cell subgroups produced during the predetermined period of time in the presence or absence of the known compound, wherein a larger proportion of the P1 and/or (P1 and P2) cell subgroups of the total number of P1 through P8 cell subgroups in the cancer cells cultured in the presence of the known compound as compared to the proportion of the P1 and/or (P1 and P2) cell subgroups of the total number of P1 through P8 cell subgroups in the cancer cells cultured in the absence of the known compound predicts the compound's ability to inhibit the multinucleate cell production resulting from post-mitotic cell fusion during DNV; and wherein the compound is identified as a treatment for cancer if the compound's ability to inhibit the multinucleate cell production resulting from post-mitotic cell fusion during DNV is greater than or equal to the known compound's ability to inhibit the multinucleate cell production resulting from post-mitotic cell fusion during DNV.

Cancers cells can be any cancer cells lines or cancer cells isolated from a patient's tumor. Many cancer cell lines are well known and readily available to one of ordinary skill in the art. By way of example and not of limitation, cancer cell lines include the human HepG2 hepatocellular carcinoma, HeLa cervical adenocarcinoma, and A549 lung adenocarcinoma.

Cancer cells can also be isolated from a patient's tumor, i.e., primary cancer cells. Typically, such cells are isolated by performing a biopsy of the patient's tumor as is known in the art. In some instances, the cancer is a solid tumor. The solid tumor can include, but is not limited to, a breast tumor, prostate tumor, brain tumor, liver tumor, head and neck tumor, colorectal tumor, lung tumor, cervical tumor, uterine tumor or thyroid tumor.

Cancer cells, whether primary metastatic or cell lines, are cultured using standard tissue culture techniques and protocols. For the in vitro method, cancer cells are cultured in the presence of a compound, whose ability to inhibit multinucleate cell production resulting from cell fusion during Daughter Number Variation in mitosis is being tested. The cells are cultured with the compound in increasing amounts in order to observe the compound's ability to inhibit multinucleate cell production. The cancer cells are also simultaneously cultured in the absence of the compound in order to have a baseline reading for the cancer cells' multinucleate cell production resulting from cell fusion during DNV in mitosis. The cancer cells are cultured in the presence and absence of the compound for a predetermined period of time, which allows for mitosis to occur.

This predetermined period typically ranges from about 24 hours to about 168 hours; however, shorter and longer periods are also contemplated. In some embodiments, the predetermined period of time is 24 hours, 48 hours, 72 hours, 96 hours, 120 hours, 144 hours, or 168 hours. 24-hour predetermined period of time is particularly useful.

During the predetermined period of time, daughter cell subgroups, herein referred to as P1 through P8, which result from mitoses with DNV are identified according to the parameters described above in terms of ploidy and post-mitotic cell fusion.

During the same time period, a total number of the mitotic cell divisions and mitotic cell divisions with DNV can also be counted. The step of measuring mitotic cell divisions (with or without DNV) can be performed by microscopy.

In any of the methods described herein, P3 through P8 cell subgroups, which are all daughter multinucleate cells that have undergone post-mitotic cell fusion can each be counted separately or they can be counted together to give a single value for P3 through P8.

The steps of identifying cell subgroups P1 through P8, and counting P1 through P8 cell subgroups can be performed by microscopy.

The microscopy used in any of the methods described herein can include time lapse and fluorescence microscopy, and more specifically, time lapse phase contrast microscopy. For example, cancer cells can be monitored by time-lapse phase contrast photographs at different positions of the plate well in which they are cultured, taken at 15-minute intervals for 24 hours at 100× magnification using the Nikon ECLIPSE Ti Live Cell Imaging Observatory. Fluorescence microscopy can be used independently or in combination with time lapse microscopy to confirm the findings. For example, cancer cells can be stained with Hoechst 33342, which is a nucleic acid stain and stains DNA, and monitored using the Nikon ECLIPSE Ti Live Cell Imaging Observatory for 24 hours, wherein the images are recorded at 15-minutes intervals and analyzed using Image J software.

The counts of P1 and P2 subgroups of cancer cells are then used to obtain their proportions based on the total number of cell subgroups P1 through P8 that resulted from mitotic DNVs during the predetermined period of time. The proportions are typically expressed as percentages. The proportion of P1 subgroup of cells is calculated as (number of P1 subgroups)÷(total number of daughter cell subgroups)×100%, and the proportion of (P1 and P2) subgroup is calculated as (number of P1 subgroups+number of P2 subgroups)÷(total number of daughter cell subgroups)×100%. This can also be expressed as (number of P1 subgroups)÷(total number of P1 through P8 subgroups)×100%, or (number of P1 subgroups+number of P2 subgroups)÷(total number of P1 through P8 subgroups)×100%, respectively.

Either P1 subgroup proportion or the sum of P1 and P2 subgroup proportions can be used in the present methods. Alternatively, both the P1 subgroup proportion and the sum of the P1 and P2 subgroup proportions can be used in the present methods.

A larger proportion of the P1 and/or (P1 and P2) subgroup cells in the cancer cells cultured in the presence of the compound as compared to the proportion of the P1 and/or (P1 and P2) subgroup cells in the cancer cells cultured in the absence of the compound predicts the compound's ability to inhibit the multinucleate cell production resulting from cell fusion during DNV. Hence, a compound that causes a larger proportion of the P1 and/or (P1 and P2) cell subgroup in the cancer cells cultured in the presence of it as compared to the proportion of the P1 and/or (P1 and P2) cell subgroups in the cancer cells cultured in the absence of the compound will be an inhibitor of multinucleate cell production resulting from cell fusion during Daughter Number Variation (DNV) in mitosis. Similarly, the larger the proportion of the P1 and/or (P1 and P2) cell subgroups resulting from the cancer cells being cultured in the presence of a compound compared to the cancer cells cultured in its absence, the greater the ability of the compound to inhibit multinucleate cell production during DNV in mitosis.

Any compound can be tested for its ability to inhibit multinucleate cell production resulting from cell fusion during DNV in mitosis.

The compound can be a known compound for treating cancer.

Compounds that are not approved for cancer treatment but possess anti-tumor properties, such as wogonin, can also be tested. Wogonin is an O-methylated flavone, a flavonoid-like chemical compound which is found in plant *Scutellaria baicalensis*.

If the compound is a known compound, the known compound can be a cytotoxic drug. For example, a cytotoxic drug can be tested for its ability to inhibit such multinucleate cell production, as indicated with 5-flurouracil (5-FU) in the Examples. Cytotoxic drugs that can be used in the present methods include, but are not limited to, 5-flurouracil, carboplatin, cisplatin, cyclophosphamide, streptozocin, methotrexate, doxorubicin, epirubicin, topotecan, etoposide, paclitaxel, docetaxel, vinblastine, and vincristine.

Alternatively, a known compound for treating cancer can be used as a comparison for a compound being tested for its ability to inhibit multinucleate cell production resulting from cell fusion during DNV in mitosis. Hence, the present disclosure provides a method for identifying a compound as a treatment for cancer if the compound's ability to inhibit the multinucleate cell production resulting from cell fusion during DNV is greater than or equal to the known compound's ability to inhibit the multinucleate cell production resulting from cell fusion during DNV. By way of example, a compound can be compared to wogonin or 5-FU.

If a compound is tested on a patient's cancer cells and found to inhibit multinucleate cell production resulting from cell fusion during DNV, the compound can then be administered to the patient. By way of example and not of limitation, any compound having its inhibitory ability at least comparable to the ability of 5-flurouracil or wogonin to inhibit the multinucleate cell production resulting from cell fusion during DNV can be administered to a patient with a tumor, in whose cancer cells the compound was tested. Thus, the present invention also provides a method of treating cancer in a patient having a tumor by administering a compound to the patient wherein the compound is identified by the above in vitro method as an inhibitor of multinucleate cell production during DNV, and thus is also identified as a treatment for cancer.

Also provided herein is a method of personalized cancer treatment for a patient having a malignant tumor, the method comprising:

culturing cancer cells in the presence or absence of a test compound for a predetermined period of time;

identifying cell subgroups P1 through P8 in DNV; and counting numbers of P1 and/or (P1 and P2) cell subgroups and P3 through P8 cell subgroups produced during the predetermined period of time in the presence or absence of the test compound, wherein a larger proportion of the P1 and/or (P1 and P2) cell subgroups of the total number of P1 through P8 cell subgroups in the cancer cells cultured in the presence of the compound as compared to the proportion of the P1 and/or (P1 and P2) cell subgroups of the total number of P1 through P8 cell subgroups in the cancer cells cultured in the absence of the test compound predicts the compound's ability to inhibit the multinucleate cell production resulting from post-mitotic cell fusion during DNV;

repeating the culturing, identifying and counting steps for one or more additional test compounds for treating cancer, and administering to the patient the test compound for treating cancer identified as having the greatest ability to inhibit the multinucleate cell production resulting from post-mitotic cell fusion during DNV in combination with at least one cytotoxic anticancer drug.

Since many cancers contain multinucleate cells, the method of personalized cancer treatment identifies test compounds that inhibit multinucleate cell production during DNV, which are then administered to cancer patients in combination with at least one cancer drug.

It is furthermore useful to identify compounds that act as inhibitors of multinucleate cell production resulting from cell fusion during DNV in the presence of one or more cancer drugs. Thus, the present disclosure also provides a method of personalized cancer treatment for a patient having a malignant tumor, the method comprising:

culturing cancer cells in the presence or absence of a test compound and at least one anticancer drug for a predetermined period of time;

identifying cell subgroups P1 through P8 in DNV; and counting numbers of P1 and/or (P1 and P2) cell subgroups and P3 through P8 cell subgroups produced during the predetermined period of time in the presence or absence of the test compound and the at least one anticancer drug, wherein a larger proportion of the P1 and/or (P1 and P2) cell subgroups of the total number of P1 through P8 cell subgroups in the cancer cells cultured in the presence of the compound and the at least one anticancer drug as compared to the proportion of the P1 and/or (P1 and P2) cell subgroups of the total number of P1 through P8 cell subgroups in the cancer cells cultured in the absence of the test compound and the at least one anticancer drug predicts the compound's ability to inhibit the multinucleate cell production resulting from post-mitotic cell fusion during DNV;

repeating the culturing, identifying and counting steps for one or more additional test compounds for treating cancer; and administering to the patient the test compound for treating cancer identified as having the greatest ability to inhibit the multinucleate cell production resulting from post-mitotic cell fusion during DNV in combination with the at least one anticancer drug.

For purposes of methods of personalized cancer treatment, cancer cells are isolated from a patient's tumor; typically, by performing a biopsy of the patient's tumor as is known in the art. The cancer can be a solid tumor. The solid tumor can include, but is not limited to, a breast tumor, prostate tumor, brain tumor, liver tumor, head and neck tumor, colorectal tumor, lung tumor, cervical tumor, uterine tumor or thyroid tumor. Since the methods of personalized cancer treatment for a patient having a malignant tumor include the steps and components already described in the in vitro methods for predicting a compound's ability to inhibit multinucleate cell production resulting from cell fusion during DNV in mitosis, those specifics are as already described in the above sections and are not repeated here.

Furthermore, the method of personalized cancer treatment allows for testing more than one test compound by repeating the steps of culturing cancers cells, identifying cell subgroups produced during DNV, and counting cell subgroups P1 and/or (P1 and P2) subgroup cells, and subgroups of multinucleate cells that have undergone post-mitotic fusion (P3 through P8) in order to identify test compounds with high ability to inhibit multinucleate cell production during DNV. The desirable test compound is then administered to a patient in combination with at least one cancer drug. For example, the cancer drug can be a cytotoxic drug.

Administration of the test compound or any cancer drug can be done as is standard in the art for purposes of the present methods. By way of example, a test compound can be administered intravascularly, intramuscularly or orally.

Tyagi I S, Chen S, Khan M A, Xie J, Li P Y, Long X, Xue H. Intrinsic and chemically-induced daughter number variations in cancer cell lines. *Cell Cycle*. 2021 March-March; 20(5-6):537-549 is incorporated herein by reference in its entirety.

EXAMPLES

To investigate DNVs, the human HepG2 hepatocellular carcinoma, HeLa cervical adenocarcinoma, and A549 lung adenocarcinoma cell lines, as well as the non-cancerous RPE1 line of hTRET-immortalized retina epithelial cells, were obtained from the American Type Culture Collection (ATCC, Manassas, Va., USA) and cultivated in Dulbecco's Modified Eagle Medium (DMEM) supplemented with 10% fetal bovine serum (Gemini Bio-Products, Sacramento. Calif.) under a humidified atmosphere of 5% $CO_2$ at 37° C. After 24 hours, the old medium was replaced by acidic DMEM growth medium buffered by 15 mM 2-(N-morpholino)-ethanesulfonic acid.HCl (MES) at pH 6.4, neutral DMEM growth medium buffered by 15 mM 3-(N-morpholino)propanesulfonic acid.HCl (MOPS) at pH 7.4, alkaline growth medium buffered by 15 mM tris(hydroxymethyl)aminomethane.HCl (Tris) at pH 8.4, or neutral DMEM growth medium containing wogonin (50 μM) or 5-FU (20 μM). Using phase contrast microscopy, time-lapse photographs were recorded at different positions of the wells at 15-minute intervals for 24 hours using the Nikon ECLIPSE Ti Live Cell Imaging Observatory, enabling the count of P1 through P8 patterns at the end of Stage 2 of the DNV process (FIG. 1). All the images were photographed at 100× magnification. Alternately, using fluorescence microscopy, the cells were seeded into 12 well plates at $1 \times 10^3$ per well and stained with Hoechst 33342 (20 bn mM, Thermofisher) for 30 minutes in an incubator at 37° C. After 30 minutes, culture medium was replaced by various treatment media and placed under the Nikon ECLIPSE Ti Live Cell Imaging Observatory for 24 hours. For the HeLa, HepG2 and A549 cells, the various treatments were also extended to 5 days. Because the RPE1 cells yielded no DNVs after 24 hours of drug treatment, its treatment periods were not extended beyond 24 hours. All the cells were manually traced and quantified using the ImageJ software. DNV frequencies were estimated by dividing the total number of multi-daughter (more than three) divisions by the total number of cell divisions. Fluorescence staining and time-lapse microscopy were employed to differentiate between the bi-, tri-, tetra- and penta-daughter cell divisions, and to estimate the percentages of the P1 through P8 patterns in the final daughter cells generated by each of the DNV events. GraphPad Prism 5.0 software was employed for statistical analysis, and the results were presented as the mean. Significance was determined using the Student t-test (two-tailed, unpaired/unequal variances).

EXAMPLES

Example 1

When HepG2 cells were cultivated at neutral pH, they gave rise to multi-daughter divisions (with more than two daughters) that amounted to 0.32% of total mitotic divisions. This percentage was changed to 1.50% at acidic pH, 0.43% at alkaline pH. 2.97% in wogonin treated cells and 0.94% in 5-FU treated cells after 24 hours (as shown in Table 1). After 5 days, it was changed to 15.5% at acidic pH, 2.40% at alkaline pH, 18.0% in wogonin treated cells and 9.30% in 5-FU treated cells after 5 days (as shown in Table 2).

TABLE 1

| Types of Divisions | Neutral pH (%) | Acidic pH (%) | Alkaline pH (%) | Wogonin (%) | 5-FU (%) |
|---|---|---|---|---|---|
| A. HepG2 Cells-24 Hours | | | | | |
| Total number of observed divisions | 2984 (100) | 2922 (100) | 3100 (100) | 2558 (100) | 2014 (100) |
| Bi-daughter | 2974 (99.6) | 2878 (98.5) | 3085 (99.5) | 2482 (97.0) | 1995 (99.1) |
| Tri-daughter | 8 (0.26) | 27 (0.92) | 11 (0.35) | 56 (2.19) | 14 (0.69) |
| Tetra-daughter | 1 (0.03) | 11 (0.38) | 4 (0.13) | 18 (0.70) | 5 (0.25) |
| ≥Tetra-daughter | 1 (0.03) | 6 (0.20) | 0 | 2 (0.08) | 0 |
| Sum of Multi daughter Divisions | 10 (0.32) | 44 (1.50)* | 15 (0.43) | 76 (2.97)* | 19 0.94)* |
| B. HeLa Cells-24 Hours | | | | | |
| Total number of observed divisions | 4872 (100) | 3818 (100) | 4249 (100) | 3094 (100) | 3296 (100) |
| Bi-daughter | 4854 (99.6) | 3749 (98.2) | 4230 (99.6) | 3041 (98.3) | 3264 (99.0) |
| Tri-daughter | 16 (0.33) | 62 (0.62) | 16 (0.38) | 47 (1.54) | 29 (0.88) |
| Tetra-daughter | 2 (0.04) | 7 (0.16) | 3 (0.01) | 6 (0.19) | 3 (0.09) |
| ≥Tetra-daughter | 0 | 0 | 0 | 0 | 0 |
| Sum of Multi daughter Divisions | 18 (0.36) | 69 (1.81) | 19 (0.44) | 53 (1.70)* | 32 (0.97)* |
| C. A549 Cells-24 Hours | | | | | |
| Total number of observed divisions | 2200 (100) | 2536 (100) | 2232 (100) | 1992 (100) | 2208 (100) |
| Bi-daughter | 2197 (99.8) | 2525 (99.6) | 2230 (99.9) | 1986 (99.6) | 2205 (99.9) |
| Tri-daughter | 3 (0.13) | 11 (0.43) | 2 (0.08) | 6 (0.30) | 3 (0.13) |
| Sum of Multi-daughter Divisions | 3 (0.13)# | 11 (0.43) | 2 (0.08) | 6 (0.3) | 3 (0.13) |
| D. RPE1 Cells-24 Hours | | | | | |
| Total number of observed divisions | 2200 (100) | 213 (100) | 2232 (100) | 106 (100) | 15 (100) |
| Bi-daughter | 2200 (100) | 213 (100) | 2232 (100) | 106 (100) | 15 (100) |
| Tri-daughter | 0 | 0 | 0 | 0 | 0 |
| Sum of multi-daughter Divisions | 0 | 0 | 0 | 0 | 0 |

*means p value <0.0001,
means p value <0.01

TABLE 2

| Types of Divisions | Acidic pH (%) | Alkaline pH (%) | Wogonin (%) | 5-FU (%) |
|---|---|---|---|---|
| A. HepG2 Cells-5 Days | | | | |
| Total Divisions | 289 (100) | 745 (100) | 312 (100) | 298 (100) |
| Bi-daughter | 244 (84.4) | 727 (97.5) | 262 (83.9) | 270 (90.6) |
| Tri-daughter | 31 (10.4) | 10 (1.3) | 50 (16.0) | 17 (5.7) |
| Tetra-daughter | 9 (3.1) | 5 (0.6) | 12 (3.8) | 8 (2.6) |
| ≥Tetra-daughter | 5 (1.7) | 3 (0.4) | 8 (2.5) | 3 (1.0) |
| Sum of Multi-daughter Divisions | 45 (15.5) | 18 (2.4) | 50 (16.0) | 28 (9.30) |

TABLE 2-continued

| Types of Divisions | Acidic pH (%) | Alkaline pH (%) | Wogonin (%) | 5-FU (%) |
|---|---|---|---|---|
| B. HeLa Cells-5 Days | | | | |
| Total Divisions | 222 (100) | 900 (100) | 245 (100) | 156 (100) |
| Bi-daughter | 195 (87.7) | 880 (97.7) | 205 (84) | 143 (91.8) |
| Tri-daughter | 24 (10.0) | 18 (2.0) | 32 (13.0) | 13 (8.3) |
| Tetra-daughter | 3 (1.3) | 2 (0.2) | 6 (2.4) | 0 |
| ≥Tetra-daughter | 0 | 0 | 2 (0.8) | 0 |
| Sum of Multi-daughter Divisions | 27 (12.1) | 10 (1.1) | 40 (16.3) | 13 (8.3) |
| C. A549 Cells-5 Days | | | | |
| Total Divisions | 289 (100) | 763 (100) | 243 (100) | 267 (100) |
| Bi-daughter | 269 (93) | 295 (98.3) | 230 (94.6) | 259 (97) |
| Tri-daughter | 19 (6.5) | 5 (0.7) | 7 (2.8) | 8 (3) |
| Tetra-daughter | 1 (0.3) | 1 (0.1) | 6 (2.4) | 0 |
| ≥Tetra-daughter | 0 | 0 | 0 | 0 |
| Sum of Multi-daughter Divisions | 20 (7.0) | 6 (0.8) | 13 (5.3) | 8 (3.0) |

Example 2

When HeLa cells were cultivated at neutral pH, they gave rise to multi-daughter divisions (with more than two daughters) that amounted to 0.36% of total mitotic divisions. This percentage was changed to 1.81% at acidic pH, 0.44% at alkaline pH, 1.70% in wogonin treated cells and 0.97% in 5-FU treated cells after 24 hours, as shown in Table 1. After 5 days, it was changed to 12.1% at acidic pH, 1.10% at alkaline pH, 16.3% in wogonin treated cells and 8.30% in 5-FU treated cells after 5 days as shown in Table 2.

Example 3

When A549 cells were cultivated at neutral pH, they gave rise to multi-daughter divisions (with more than two daughters) that amounted to 0.13% of total mitotic divisions. This percentage was changed to 0.43% at acidic pH, 0.08% at alkaline pH, 0.30% in wogonin treated cells and 0.13% in 5-FU treated cells after 24 hours (Table 1) After 5 days, it was changed to 7.0% at acidic pH, 0.80% at alkaline pH, 5.3% in wogonin treated cells and 3.0% in 5-FU treated cells after 5 days (Table 2).

Example 4

Growth of HepG2, HeLa and A549 cells at different pHs or treatment with wogonin or 5-FU caused dissimilar responses in the different cells after 24 hours. For HepG2 cells, the P1% was 23.0% at neutral pH, 25.0% at acidic pH, 5.8% at alkaline pH, 42.8% when treated with wogonin, and 17.6% when treated with 5-FU. For HeLa cells, the P1% was 23.8% at neutral pH, 32.2% at acidic pH, 9.0% at alkaline pH, 51.6% when treated with wogonin, and 76.9% when treated with 5-FU. For A549 cells, the P1% was 33.3% at neutral pH or acidic pH, 50.0% at alkaline pH, 57.1% when treated with wogonin, and 100% when treated with 5-FU.

Example 5

After 24 hours, for HepG2 cells, the (P1+P2)% was 34.6% at neutral pH, 43.1% at acidic pH, 23.5% at alkaline pH, 60.3% when treated with wogonin, and 35.2% when treated with 5-FU. For HeLa cells, the (P1+P2)% was 47.6% at neutral pH, 45.1% at acidic pH, 31.8% at alkaline pH, 61.2% when treated with wogonin, and 92.3% when treated with 5-FU. For A549 cells, the (P1+P2)% was 33.3% at neutral pH or acidic pH, 100% at alkaline pH, 57.1% when treated with wogonin, and 100% when treated with 5-FU. See Table 4 below.

The fact that the HepG2, HeLa and A549 cancer cells engaged in DNV formation, but the non-cancerous RPE1 cells did not do so (Table 1) indicated that DNVs were exclusively or mainly a manifestation of the cancerous state of cells. Furthermore, the severely cancerous HepG2 and Hela cells produced more DNVs than the A549 cells, which after prolonged propagation in vitro had reverted partially to a differentiated Type II pneumocyte phenotype with multi-lamellar body (MLB) development (Cooper et al. *PLoS One.* 2016 Oct. 28; 11(10):e0164438), suggesting that DNV represented a phenotype of malignancy, and the A549 cells were less malignant than HepG2 and HeLa. Moreover, the production of up to penta-daughters by HepG2, up to only tetra-daughters by HeLa, and up to only tri-daughters by A549 after 24 hours of treatment pointed to HepG2 and HeLa being more aggressive than A549, and HepG2 being more aggressive than HeLa under wogonin treatment (Table 3). Table 3 shows statistical p-values pertaining to percentage of DNVs in HepG2, HeLa or A549 cells under treatment with acidic pH, alkaline pH, wogonin or 5FU relative to percentage of DNVs at neutral pH and inequality of the percentages of DNVs under wogonin versus 5-FU treatments in part (A), and inequality between different cell lines under various treatment conditions in part (B). The numbers of DNVs and total cell divisions were those observed after various treatments for 24 hours as shown in Table 1. 'ns' represents 'no significant difference'.

TABLE 3

A

| | Acidic pH | Alkaline PH | Wogonin | 5-FU | Wogonin > 5-FU |
|---|---|---|---|---|---|
| HepG2 | <0.0001 | <0.0001 | 0.0003 | 0.0001 | |
| HeLa | <0.0001 | ns | <0.0001 | <0.0001 | ns |
| A549 | 0.022 | ns | is | ns | ns |

B

| | Neutral pH | Acidic pH | Alkaline pH | Wogonin | 5-FU |
|---|---|---|---|---|---|
| HepG2 > HeLa | ns | ns | ns | 0.003 | ns |
| HepG2 > A549 | ns | 0.0135 | 0.001 | 0.0001 | 0.002 |
| HeLa > A549 | ns | 0.044 | 0.0447 | 0.008 | 0.0002 |

TABLE 4

Numbers of different daughter-cell subgroups and their percentages among all the P1 through P8 subgroups in mitoses with DNV.

| Cell line | Treatment | \multicolumn{9}{c}{Numbers of different daughter cell subgroups in mitoses with DNV (%)} | Mitoses with DNV |
|---|---|---|---|---|---|---|---|---|---|---|---|
| | | P1 | P2 | P1 + P2 | P3 | P4 | P5 | P6 | P7 | P8 | |
| HepG2 | Neutral pH | 6 (23.0) | 3 (11.5) | 9 (34.6) | 5 (19.2) | 5 (19.2) | 1 (3.8) | 2 (7.6) | 2 (7.6) | 2 (7.6) | 26 |
| | Acidic pH | 22 (25.0) | 16 (18.1) | 38 (43.1) | 17 (19.3) | 8 (9.0) | 13 (14.7) | 10 (11.3) | 2 (2.2) | 0 | 88 |
| | Alkaline pH | 1 (5.8) | 3 (17.6) | 4 (23.5) | 7 (41.1) | 2 (11.7) | 2 (11.7) | 0 | 2 (11.7) | 0 | 17 |
| | Wogonin | 27 (42.8) | 11 (17.4) | 38 (60.3) | 8 (12.7) | 9 (14.2) | 3 (4.7) | 3 (4.7) | 2 (3.1) | 0 | 63 |
| | 5-FU | 3 (17.6) | 3 (17.6) | 6 (35.2) | 6 (35.2) | 0 | 2 (11.7) | 3 (17.6) | 0 | 0 | 17 |
| | Total | 59 (27.9) | 37 (17.5) | 96 (45.4) | 42 (19.9) | 24 (11.3) | 21 (9.9) | 18 (8.5) | 8 (3.7) | 2 (0.9) | 211 |
| HeLa | Neutral pH | 5 (23.8) | 5 (23.8) | 10 (47.6) | 3 (14.2) | 0 | 1 (4.7) | 6 (28.5) | 0 | 1 (4.7) | 21 |
| | Acidic pH | 10 (32.2) | 4 (12.9) | 14 (45.1) | 7 (22.5) | 1 (3.2) | 4 (12.9) | 5 (16.1) | 0 | 0 | 31 |
| | Alkaline pH | 2 (9.0) | 5 (22.7) | 7 (31.8) | 9 (40.9) | 0 | 2 (9.0) | 3 (13.6) | 0 | 1 (4.5) | 22 |
| | Wogonin | 16 (51.6) | 3 (9.6) | 19 (61.2) | 10 (32.2) | 2 (6.4) | 0 | 0 | 0 | 0 | 31 |
| | 5-FU | 10 (76.9) | 2 (15.3) | 12 (92.3) | 1 (7.6) | 0 | 0 | 0 | 0 | 0 | 13 |
| | Total | 43 (36.4) | 19 (16.1) | 62 (52.5) | 30 (25.4) | 3 (2.5) | 7 (5.9) | 14 (11.8) | | 2 (1.6) | 118 |
| A549 | Neutral pH | 1 (33.3) | 0 | 1 (33.3) | 2 (66.6) | 0 | 0 | 0 | 0 | 0 | 3 |
| | Acidic pH | 3 (33.3) | 0 | 3 (33.3) | 4 (44.4) | 0 | 1 (11.1) | 1 (11.1) | 0 | 0 | 9 |
| | Alkaline pH | 1 (50.0) | 1 (50.0) | 2 (100.0) | 0 | 0 | 0 | 0 | 0 | 0 | 2 |
| | Wogonin | 4 (57.1) | 0 | 4 (57.1) | 3 (42.8) | 0 | 0 | 0 | 0 | 0 | 7 |
| | 5-FU | 3 (100) | 0 | 3 (100) | 0 | 0 | 0 | 0 | 0 | 0 | 3 |
| | Total | 12 (50.0) | 1 (4.1) | 13 (54.1) | 9 (37.5) | 0 | 1 (4.1) | 1 (4.1) | 0 | 0 | 24 |

Example 6: Cell Cytotoxicity Assay

Figure 7:
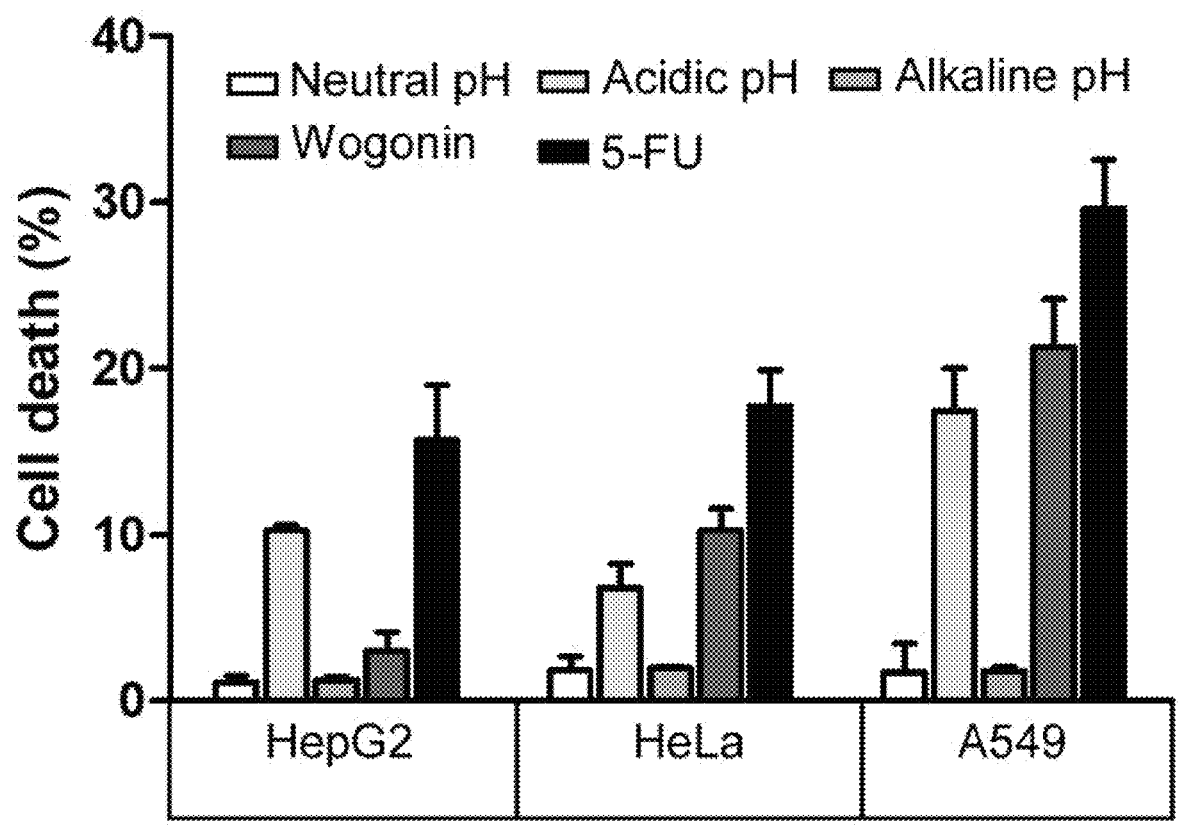
FIG. 7 shows cell death of cancer cell lines in different culture conditions. Cell cytotoxicity assay was carried out on 96 well plate, where cells were treated with neutral, acidic, alkaline pH and anti-cancer drug wogonin or 5-FU. After 24 hours, crystal violet (8% in methanol), and dye absorbed by live cells was extracted with sodium citrate (0.1 M) in 50% ethanol. Absorbance was read at 600 nm.
Figure 8:
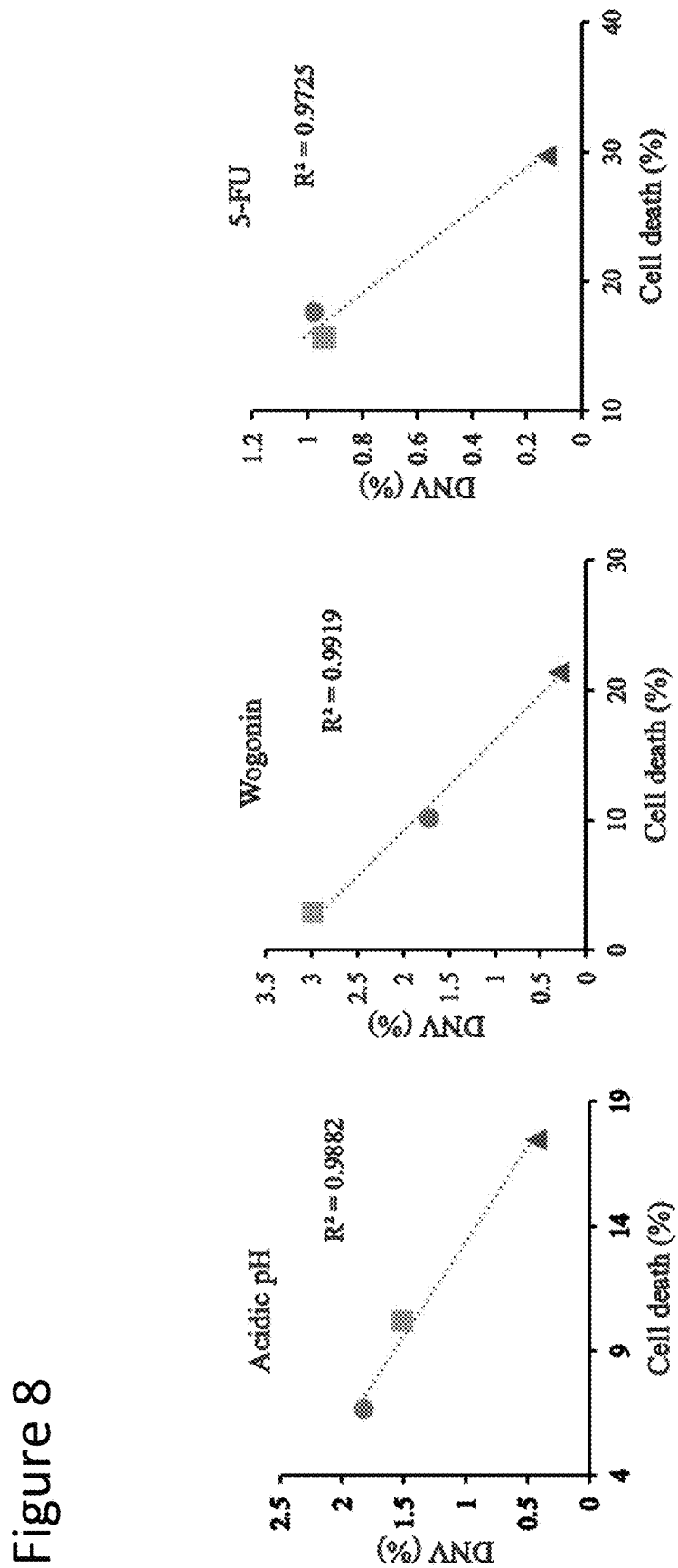
FIG. 8 depicts correlation between cell death and DNV frequencies. The graphs show HepG2 (orange), HeLa (green) and A549 (red) cells upon acidic pH (left) wogonin (middle) and 5-FU (right) treatment.

HepG2, HeLa and A549 cells were grown to a monolayer density of 1×103 per well in neutral growth medium overnight. There upon the cells were changed to various treatment media at neutral, acidic and alkaline pHs, neutral medium containing 50 µM wogonin and neutral medium containing 20 µM 5-FU, for 24 hours at 37° C. in humidified 5% CO2 atmosphere. Following the treatment, floating cells were removed, and the attached cells were stained with crystal violet (8% in methanol); the dye absorbed by the live cells was extracted with sodium citrate (0.1 M) in 50% ethanol [1 25], and quantitated by absorbance at 600 nm. As expected, 5-FU and wogonin increased cell death in all three cancer cell lines HepG2, HeLa and A549 as compared to neutral pH, with 5-FU having a greater effect than wogonin (FIG. 7).

It is to be understood that this invention is not limited to particular embodiments described, as such may, of course, vary. It is also to be understood that the terminology used herein is for the purpose of describing particular embodiments only, and is not intended to be limiting, since the scope of the invention will be limited only by the appended claims.

What is claimed is:

1. A method of treating cancer in a patient having a malignant tumor, the method comprising administering a compound to the patient, provided that the compound is determined to inhibit multinucleate cell production resulting from cell fusion during a process of Daughter Number Variation (DNV) in mitosis in an in vitro method, wherein the method comprises:

culturing cancer cells in the presence or absence of the compound for a predetermined period of time;

identifying cell subgroups P1 through P8 in DNV; and counting numbers of P1, and/or P1 and P2 cell subgroups and P3 through P8 cell subgroups produced during the predetermined period of time in the presence or absence of the compound, wherein a larger proportion of the P1 and/or P2 cell subgroups of the total number of P1 through P8 cell subgroups in the cancer cells cultured in the presence of the compound as compared to the proportion of the P1, and/or P1 and P2 cell subgroups of the total number of P1 through P8 cell subgroups in the cancer cells cultured in the absence of the compound determines the compound's ability to inhibit the multinucleate cell production resulting from post-mitotic cell fusion during DNV, wherein P1 cell subgroups are single mononucleate cells, P2 cell subgroups are clusters of one binucleate cell and two mononucleate cells, P3 cell subgroups are clusters of one multinucleate cell with two nuclei and one mononucleate cell, P4 cell subgroups are one multinucleate cell with three nuclei, P5 cell subgroups are clusters of either two multinucleate cells with two nuclei or one multinucleate cell with two nuclei and one binucleate cell, P6 cell subgroups are clusters of one multinucleate cell with three nuclei and one mononucleate cell, P7 cell subgroups are one multinucleate cell with four nuclei, and P8 cell subgroups are one multinucleate cell with five nuclei; and wherein P1 and P2 cell subgroups have not undergone post-mitotic cell fusion and P3 through P8 cell subgroups have undergone post-mitotic cell fusion.

2. The method of claim 1, wherein the cancer cells comprise HepG2, HeLa, or A549 cancer cells.

3. The method of claim 1, wherein the cancer cells comprise cancer cells isolated from a patient's tumor.

4. The method of claim 3, wherein the tumor is a solid tumor.

5. The method of claim 4, wherein the solid tumor comprises a breast tumor, prostate tumor, brain tumor, liver tumor, head and neck tumor, colorectal tumor, lung tumor, cervical tumor, uterine tumor or thyroid tumor.

6. The method of claim 1, wherein the predetermined period of time ranges from about 24 hours to about 168 hours.

7. The method of claim 6, wherein the predetermined period of time is 24 hours.

8. The method of claim 6, wherein the predetermined period of time is 24 hours, 48 hours, 72 hours, 96 hours, 120 hours, 144 hours, or 168 hours.

9. The method of claim 1, wherein the steps of identifying cell subgroups and counting cell subgroups are performed by microscopy.

10. The method of claim 9, wherein the microscopy comprises time lapse microscopy or fluorescence microscopy.

11. The method of claim 1, wherein the compound is cytotoxic to the cancer cells.

12. The method of claim 3, wherein the compound's augments, through inhibition of post-mitotic cell fusions and the generation of multinucleate daughter cells from such fusions in DNV, the efficacy of treatment of the tumor by either a cytotoxic chemotherapeutic agent or physical means.

13. The method of claim 1,
wherein the compound's ability to inhibit the multinucleate cell production resulting from post-mitotic cell fusion during DNV is at least comparable to the ability of 5-fluorouracil to inhibit the multinucleate cell production resulting from post-mitotic cell fusion during DNV.

14. The method of claim 1,
wherein the compound's ability to inhibit the multinucleate cell production resulting from post-mitotic cell fusion during DNV is at least comparable to the ability of wogonin to inhibit the multinucleate cell production resulting from post-mitotic cell fusion during DNV.

15. The method of claim 1, wherein the in vitro method further comprises:

culturing cancer cells in the presence or absence of a known compound for treating cancer for a predetermined period of time;

identifying cell subgroups P1 through P8 in DNV; and counting numbers of P1 and/or P1 and P2 cell subgroups and P3 through P8 cell subgroups produced during the predetermined period of time in the presence or absence of the known compound, wherein a larger proportion of the Ph and/or P1 and P2 cell subgroups of the total number of P1 through P8 cell subgroups in the cancer cells cultured in the presence of the known compound as compared to the proportion of the P1 and/or P1 and P2 cell subgroups of the total number of P1 through P8 cell subgroups in the cancer cells cultured in the absence of the known compound predicts the compound's ability to inhibit the multinucleate cell production resulting from post-mitotic cell fusion during DNV; and wherein the compound is determined to treat cancer if the compound's ability to inhibit the multinucleate cell production resulting from post-mitotic cell fusion during DNV is greater than or equal to the known compound's ability to inhibit the multinucleate cell production resulting from post-mitotic cell fusion during DNV.

16. The method of claim 15, wherein the known compound for treating cancer comprises 5-fluorouracil.

17. The method of claim 15, wherein the known compound for treating cancer comprises wogonin.

18. The method of claim 15, further comprising administering to the patient the compound identified as a treatment for cancer in combination with a cytotoxic anticancer drug.

19. The method of claim 1, wherein the cancer cells are isolated from the malignant tumor and the in vitro method further comprises:

repeating the culturing, identifying and counting steps for one or more additional compounds; and administering to the patient the compound determined as having the largest proportion of the P1, and or P1 and P2 cell subgroups to the total number of P1 through P8 cell subgroups wherein the compound is administered in combination with at least one anticancer drug.

20. The method of claim 19, wherein, in the in vitro method, the cancer cells isolated from the malignant tumor are cultured in the presence or absence of the compound and at least one anticancer drug for the predetermined period of time; and the counting numbers of the P1, and/or P1 and P2 cell subgroups and P3 through P8 cell subgroups produced during the predetermined period of time in the presence or absence of the compound and the at least one anticancer drug, wherein a larger proportion of the P1, and/or P1 and P2 cell subgroups of the total number of P1 through P8 cell subgroups in the cancer cells cultured in the presence of the compound and the at least one anticancer drug as compared to the proportion of the P1, and/or P2 cell subgroups of the total number of P1 through P8 cell subgroups in the cancer cells cultured in the absence of the compound and the at least one anticancer drug predicts the compound's ability to inhibit the multinucleate cell production resulting from post-mitotic cell fusion during DNV.

* * * * *

UNITED STATES PATENT AND TRADEMARK OFFICE
CERTIFICATE OF CORRECTION

Page 1 of 1

PATENT NO. : 11,952,593 B2
APPLICATION NO. : 17/495768
DATED : April 9, 2024
INVENTOR(S) : Hong Xue It is certified that error appears in the above-identified patent and that said Letters Patent is hereby corrected as shown below:

In the Claims

Column 19 Line 43 should read – The method of claim 3, wherein the compound –.

Signed and Sealed this
Fourth Day of February, 2025

Coke Morgan Stewart
*Acting Director of the United States Patent and Trademark Office*